United States Patent [19]

Twardowski et al.

[11] Patent Number: 5,209,723
[45] Date of Patent: May 11, 1993

[54] MULTIPLE LUMEN CATHETER FOR HEMODIALYSIS

[75] Inventors: Zbylut J. Twardowski; John C. Van Stone; W. Kirt Nichols, all of Columbia, Mo.

[73] Assignee: The Curators of the University of Missouri, Columbia, Mo.

[21] Appl. No.: 772,613

[22] Filed: Oct. 8, 1991

Related U.S. Application Data

[63] Continuation of Ser. No. 461,684, Jan. 8, 1990, abandoned.

[51] Int. Cl.$^5$ .............................................. A61M 3/00
[52] U.S. Cl. ........................................ 604/43; 604/96; 604/280; 604/281
[58] Field of Search ................. 604/101, 102, 27, 29, 604/35, 39, 43, 96, 264, 266, 268, 280, 281, 283; 606/194

[56] References Cited

U.S. PATENT DOCUMENTS

| | | |
|---|---|---|
| 3,612,038 | 10/1971 | Halligan . |
| 3,890,977 | 6/1975 | Wilson . |
| 3,935,857 | 2/1976 | Co . |
| 4,117,836 | 10/1978 | Erikson . |
| 4,292,976 | 10/1981 | Banka . |
| 4,385,631 | 5/1983 | Uthmann .............................. 604/43 |
| 4,392,855 | 7/1983 | Oreopoulos et al. . |
| 4,531,933 | 7/1985 | Norton et al. . |
| 4,568,329 | 2/1986 | Mahurkar . |
| 4,681,564 | 7/1987 | Landreneau .......................... 604/29 |
| 4,681,570 | 7/1987 | Dalton .................................. 604/281 |
| 4,687,471 | 8/1987 | Twardowski et al. . |
| 4,694,838 | 9/1987 | Wijayarthna et al. . |
| 4,701,159 | 10/1987 | Brown et al. . |
| 4,735,620 | 4/1988 | Ruiz . |
| 4,772,269 | 9/1988 | Twardowski et al. . |
| 4,790,809 | 12/1988 | Kuntz . |
| 4,834,709 | 5/1989 | Banning et al. . |
| 4,846,814 | 7/1989 | Ruiz . |
| 4,867,742 | 9/1989 | Calderon ............................. 604/101 |
| 4,895,561 | 1/1990 | Mahurker ............................ 604/43 |
| 4,935,004 | 6/1990 | Cruz ..................................... 604/29 |
| 4,961,731 | 10/1990 | Bodicky et al. . |
| 4,985,014 | 1/1991 | Orejola ................................ 604/43 |
| 5,016,640 | 5/1991 | Ruiz . |
| 5,053,023 | 10/1991 | Martin ................................. 604/280 |

FOREIGN PATENT DOCUMENTS 0132344  1/1985  European Pat. Off. ............ 604/281

OTHER PUBLICATIONS

Brochure by Quinton Instrument Company entitled Instructions for Use Catheter Repair Kits-2 pages.

Primary Examiner—John D. Yasko
Assistant Examiner—Anthony Gutowski
Attorney, Agent, or Firm—Gerstman & Ellis

[57] ABSTRACT

A multiple lumen, intravenous catheter for hemodialysis or the like defines a distal end portion in which at least a pair of the catheter lumens each communicates with the exterior through aperture means. By this invention the aperture means of one of the lumens defines a first port at essentially the distal catheter end, and the aperture means of the other of the lumens defines a second port spaced proximally along the catheter from the distal end and first port. The second port is positioned to face radially inwardly to at least a slight degree to avoid engagement of the wall of the blood vessel that the catheter occupies. Additionally, the tip of the catheter distal of the second port is preferably of substantially helically shape, being sized to assist in keeping the second port away from the blood vessel wall. As another feature, the catheter may be angled in its as-manufactured, unstressed condition to avoid pressing by elastic memory against internal blood vessel walls. Also, the catheter may define an inflatable balloon positioned between the first and second ports as a means for spacing particularly the second port away from blood vessel walls.

17 Claims, 2 Drawing Sheets

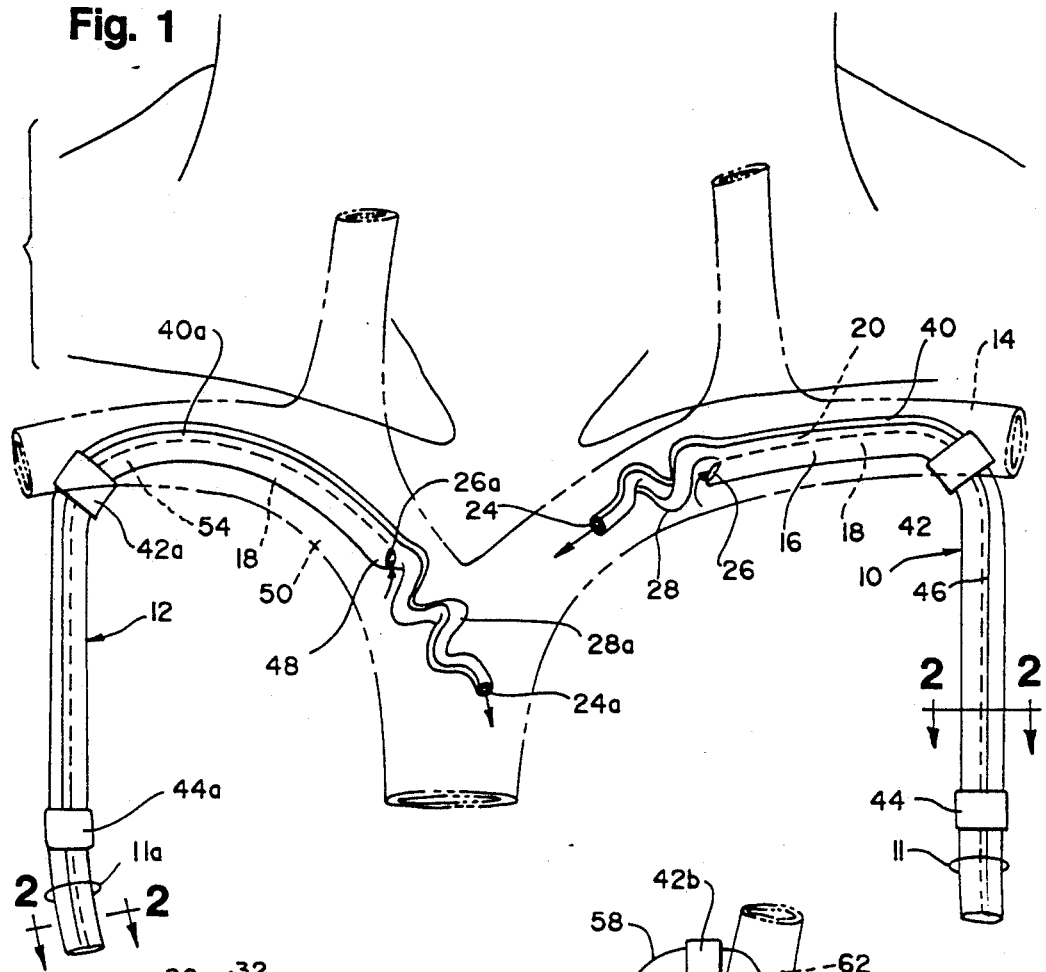
Fig. 1
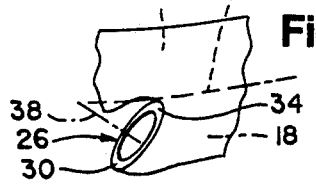
Fig. 1A
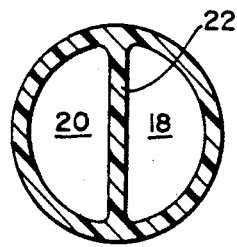
Fig. 2
Fig. 3

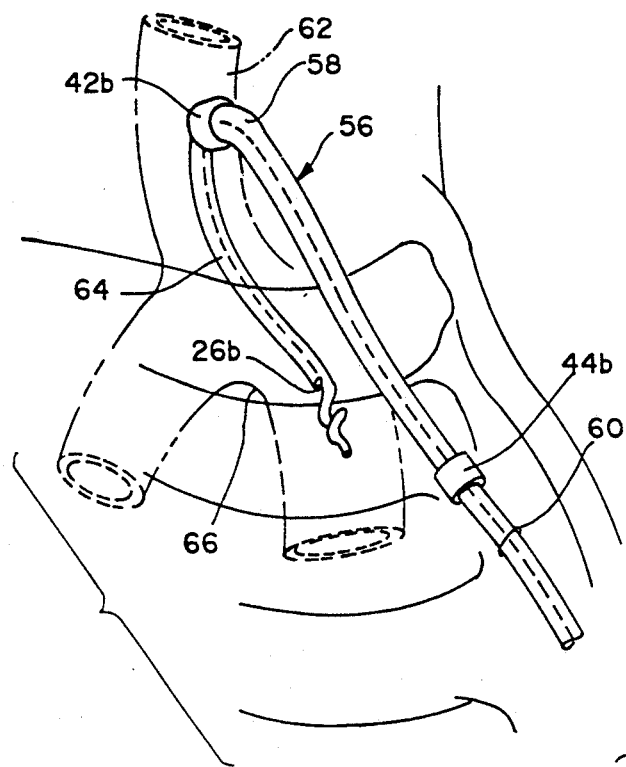
Fig. 4
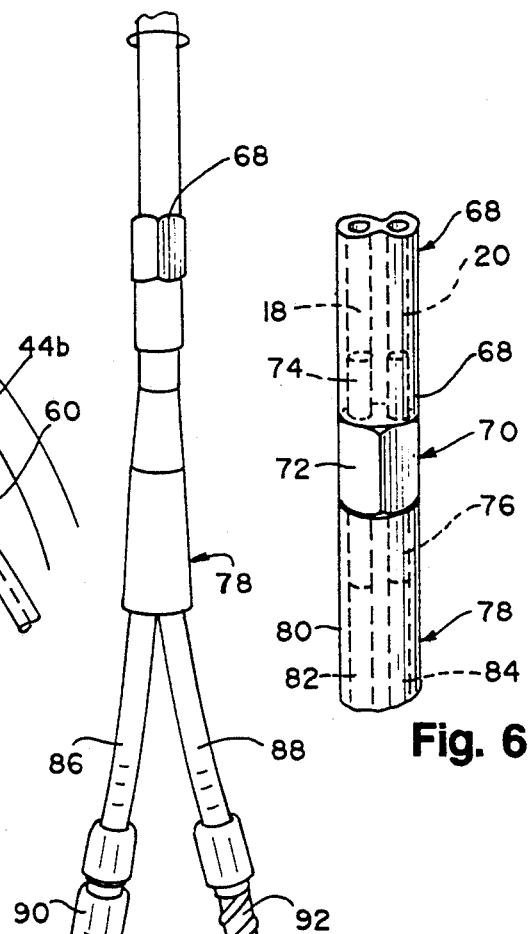
Fig. 5
Fig. 6
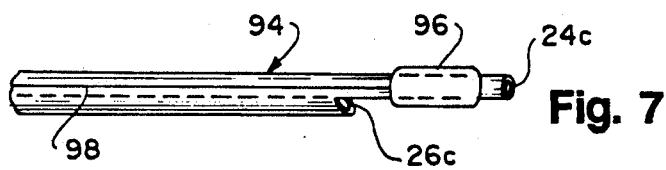
Fig. 7
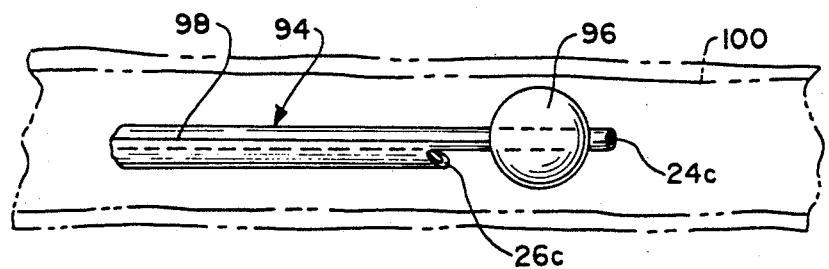
Fig. 8

5,209,723

MULTIPLE LUMEN CATHETER FOR HEMODIALYSIS

CROSS REFERENCE TO RELATED APPLICATION

This is a continuation of Twardowski et al. application Ser. No. 461,684, filed Jan. 8, 1990 (now abandoned).

BACKGROUND OF THE INVENTION

Double lumen catheters have been used as permanent blood access devices for easy and safe access to a patient's arteriovenous system for hemodialysis. Such double lumen catheters have been clinically used and commercially sold. One example of such double lumen catheters is disclosed in Mahurkar U.S. Pat. No. 4,568,329, with other examples of such catheters being disclosed as cited references in that patent.

The use of an indwelling hemodialysis catheter has significant advantages. Particularly, the patient does not have to endure a needle puncture to gain access to his arteriovenous system in every dialysis procedure, but, rather, the indwelling catheter can be simply periodically hooked up to the dialyzer system to provide a blood flow path between the patient and the dialyzer system.

However, as a disadvantage, indwelling catheters which connect to the arteriovenous system are subject to risks of infection and clotting.

Additionally, with a multiple lumen catheter, one lumen serves as a blood outflow path from the arteriovenous (A.V.) system and another lumen serves as an inflow passage for blood to be returned to the A.V. system. As a continuing problem with multiple lumen hemodialysis catheters, the suction at the entrance of the outflow port through which blood flows can cause the outflow port to be occluded by intimal tissues within the vein This, in turn, can cause tissue damage and results in clotting, which has significantly limited the use of multiple lumen indwelling catheters for hemodialysis.

Furthermore, most multiple-lumen hemodialysis catheters are semi-rigid, with a result that they cannot be anchored securely, and consequently are prone to piston-like movements while they indwell a vein. This movement inside the vein tends to further irritate the intima of the vein wall tissue, leading to further clot formation and vein inflammation. Likewise, outward movements of the subcutaneous and external segments of such a catheter tend to collect contaminants, and to infect the subcutaneous tunnel through the tissue as these segments once again move inwardly.

Other hemodialysis catheters are more flexible, but are molded and cured in a generally straight configuration. Such catheters, however, are usually installed into the venous system in a substantially curved position. Thus, the elastic memory of these catheters causes them to press against some of the vein intima in certain places, with a resulting irritation thereof, and an increase in clotting potential.

By this invention, a multiple-lumen, intravenous catheter, particularly for hemodialysis and also for any other desired use, is provided. The outflow port of the catheter, where a suction is developed, is protected against engagement with the vein intima tissues and the like.

Additionally, the catheter of this invention may be of a desired, curved configuration in its as-manufactured, unstressed configuration, so that the catheter occupies its indwelling site with less irritation of the vein or duct walls, wherever the catheter may be emplaced. The result of this is a catheter which is less likely to generate blood clotting or tissue irritation, and also with a reduction in its potential for causing infection. Such an indwelling catheter may thus be carried by a patient on hemodialysis for long-term use, providing the patient with relief from the anxiety and pain of the normal and frequent needle sticks that are required to accomplish hemodialysis with an A.V. fistula, and facilitating the hemodialysis procedure in other ways as well.

DESCRIPTION OF THE INVENTION

By this invention, a multiple lumen catheter for hemodialysis or the like is provided. The catheter has a distal end portion in which at least a pair of the catheter lumens each communicate with the exterior through aperture means.

In accordance with this invention, the aperture means of one of the lumens defines a first port at essentially the distal catheter end. The aperture means of the other of the lumens defines a second port spaced proximally along the catheter from the distal end and first port. In one embodiment, the second port is defined by a substantially angular wall which has a radially outer portion relative to the catheter axis that is positioned slightly closer to the catheter distal end than a radially inner portion of the same substantially angular wall. The result of this is that the second port faces radially inwardly to a degree, with the axis of the second port being angled radially inwardly at an acute angle to the catheter axis.

By this means, the second port, which is preferably used as the suction port for withdrawing blood through the catheter for the hemodialyzer or other medical device, operates with a significant reduction of possibility that intimal tissue along the blood vessel walls may be captured by suction at the second port. This protects the delicate intimal tissues, and reduces the possibility of clotting, irritation, and infection, while still providing an adequately-sized aperture to draw blood into the catheter for processing by medical apparatus.

The blood is then typically returned through the lumen that connects with the first port, the first port being longitudinally spaced from the second port so that returning blood can be distributed away from the second, suction port, to minimize immediate recycling of the processed blood.

Further in accordance with this invention, the one lumen which connects with the first port comprises a portion that extends distally beyond the second port. This one lumen portion which extends distally beyond the second port is preferably defined by a distal catheter portion which is of substantially helical shape. Such a helical catheter portion can serve to generally keep the distal end of the catheter away from the sides of the vein walls (or other blood vessel or duct walls as the case may be), particularly when the diameter of the helical section exceeds the catheter diameter. As the result of this, particularly the second port and also the first port may be held in spaced relation from the blood vessel walls. Thus this helical catheter portion is an alternative or additional means for preventing suction of the blood vessel intima into the second port.

Also, the catheters of this invention preferably have a section thereof which defines an angle of at least about 90 degrees, and, if desired, up to about 180 degrees. This angled section is preferably spaced from and proximal to the second port. As additional embodiment, a length of such a catheter which is positioned between the angled section and the second port defines an arc in the dimension perpendicular to the plane defined by the angle in the section. Both the angled section and the arc may be proportioned so that the flexible catheter, in its unstressed, as-manufactured configuration, can provide improved registry with the shape of the blood vessel in which the length of the catheter resides. Thus, such a catheter will exhibit less pressure and abrasion against the blood vessel walls, providing conditions under which less clotting and tissue irritation will take place. This, in turn, provides a catheter which is capable of long-term indwelling in the A.V. system of a patient.

As another modification, the catheter of this invention may define an inflatable balloon positioned between the first and second ports. The balloon may be inflatable to a size which is large enough to limit engagement of the second port with a wall of the blood vessel (or duct) in which the catheter resides, but which is small enough to avoid complete occlusion of the blood vessel or duct. Additionally, a conventional inflation lumen may be provided in the catheter, with the inflation lumen communicating with the balloon to permit inflation and deflation thereof from a fluid source at the proximal end of the catheter. By this means, the balloon can serve to approximately center the first and second ports from vessel or duct walls, which is particularly desirable with respect to the second port for the reasons described above.

The catheter of this invention may comprise a pair of tubular connector extensions positioned at the proximal end of the catheter. These extensions carry conventional connectors at their ends opposed to their connection with the catheter, to facilitate connection with a medical device such as a hemodialyzer. Double-ended tubular prong means are provided, connecting each of the tubular extensions with one of the catheter lumens through which circulating blood flow is intended to take place.

The advantage of such an structure is that the external, proximal catheter end portions such as the connectors tend to wear with use. If the catheter of this invention is a true, long-term, indwelling catheter, the proximal connectors may wear out before the distal end of the catheter. Thus, by this invention, the double lumen catheter may be cut outside of the body at its proximal end, and a new pair of tubular connector extensions and double ended tubular prong means may be installed, to permit continued use of the indwelling catheter. To accommodate this, the indwelling catheter may extend outside of the body for several inches, to permit several cuttings of the catheter and replacements of tubular connector extensions before the entire catheter must be replaced.

While the aperture means of the respective flow lumens of this catheter may utilize a plurality of side ports as a supplement to or substitute for the end-mounted first and second ports, such is generally deemed undesirable for the following reason:

Between usages, the indwelling catheter of this invention exhibits stagnant flow conditions within its respective lumens. Such flow conditions are of course conducive to blood clotting, so, typically, such a catheter is filled with heparin solution between usages. The presence of side ports will tend to increase the diffusion and replacement of the heparin with blood between catheter usages, which can increase the possibility that clotting can take place in the blood which finds its way into the catheter lumens and then sits in a stagnant manner. The use of single, first and second ports in the manner described herein can reduce this possibility.

DESCRIPTION OF DRAWINGS

In the drawings, FIG. 1 is a diagrammatic view of a pair of multiple-lumen, I.V. catheters of this invention, each shown to be installed in, respectively, the right or left brachiocephalic vein through the respective subclavian veins, a distal portion of each catheter only being shown;

FIG. 1a is an enlarged, fragmentary, perspective view of a portion of one of the catheters of FIG. 1.

FIG. 2 is an enlarged, sectional view taken along each of lines 2—2 of FIGS. 1;

FIG. 3 is an elevational view of an indwelling catheter in accordance with this invention, implanted into a brachiocephalic vein through the right internal jugular vein, with only a distal portion of the catheter being shown;

FIG. 4 is an elevational view similar to FIG. 3, but rotated approximately 90 degrees about the vertical axis;

FIG. 5 is an elevational view of the proximal portion of the catheters illustrated in FIGS. 1–4;

FIG. 6 is an enlarged, elevational view, showing internal structure, of the junction between the intravenous catheter of this invention and the pair of tubular extensions thereof carried at the proximal catheter end;

FIG. 7 is an elevational view of the distal end of another embodiment of the catheter of this invention; and FIG. 8 is an elevational view similar to FIG. 7, but showing the catheter emplaced in a blood vessel and with the balloon fully inflated.

DESCRIPTION OF SPECIFIC EMBODIMENTS

Referring to the drawings, FIG. 1 shows the outline of an human upper torso, shoulders, and neck, and some of the major veins of the area, in phantom, with two multiple lumen I.V. catheters of this invention shown to be emplaced in indwelling manner. This arrangement is primarily for purposes of illustration since, under normal circumstances, no more than one indwelling catheter will be implanted in a patient at one time.

Double-lumen indwelling catheters 10, 12 may be made of a flexible plastic material such as silicone or polyurethane elastomers, defining a double lumen in the manner of FIG. 2.

Catheter 10 extends through a surgically formed tissue tunnel from an entry port 11 at the skin, through to an aperture cut in vein 14, at which point catheter 10 defines an angle of approximately 90 degrees and a vein indwelling portion 16.

Catheter 10 defines a pair of lumens 18, 20, which are separated by a partition 22. Lumen 20 extends to the distal end of catheter 10 and terminates in a first open port 24, while lumen 18 terminates in a second port 26, port 26 being spaced proximally along catheter 10 from the distal end and first port 24. Additionally, as shown, the portion 28 that extends distally beyond second port 26 is of substantially helical shape, the helical shape being of a diameter slightly larger than the catheter diameter to help prevent second port 26 from engaging the walls of vein 14 and sucking intima as previously described. At the same time, an open flow path is readily available for blood to pass through second port 26 and along lumen 18 through the catheter into a hemodialyzer or the like.

After the hemodialysis of the particular blood portion has been completed, it is returned through lumen 20 of catheter 10, to be expelled out of the distal end thereof through first port 24, so that the expelled blood is longitudinally separated from blood intake port 26, to reduce shunting of processed blood back into the intake port.

Further in accordance with this invention, as particularly shown in the detailed FIG. 1A, second port 26 is defined by a substantially angular wall having a radially outer portion 30, relative to the catheter central axis 32, that is positioned slightly closer to the distal end 24 of catheter than a radially inner portion 34 of the substantially angular wall. Thus the axis 38 of second port 26 is angled radially inwardly at an acute angle to catheter axis 32. As previously stated, the effect of this is to cause second port 26 to be less likely to suck in vein wall intima along with inflowing blood, to avoid tissue damage and consequent clotting or vein irritation.

Catheter 10 is shown in its as-formed, unstressed configuration, although being flexible, it can be straightened out for insertion and packaging. However, because catheter 10 defines an angled section, it can fit into vein 14 without any significant plastic memory attempting to force the catheter into a straight configuration or the like, so that the distal portion 16 of the catheter resides in the vein with less pressure against the vein walls.

Catheter 10 also carries a radiopaque stripe 40 to facilitate location of the catheter by a fluoroscope. Similarly, catheter 10 carries a pair of spaced fabric cuffs 42, 44, being spaced approximately four centimeters apart and adapted to be a site for tissue ingrowth, for long-term securance of catheter 10 in its indwelling position as shown. Both cuffs reside in the tunnel formed through the tissue by the surgeon, with the outer cuff 44 being positioned approximately one centimeter from tunnel exit 11. Catheter portion 46 which resides in the surgical tunnel is preferably directed downwardly, so that tunnel exit contamination such as sweat, dirt, and water tends to stay out of tunnel exit 11, and internal drainage also is facilitated through the tunnel exit. Also, although upper portions of the catheter are near the neck of the patient, the tunnel exit 11 is substantially below the neck in such a configuration.

Accordingly, such an implanted indwelling catheter can remain with the patient for a long period of time, freeing him from the agony of frequent punctures by large needles as normally required in dialysis procedures, while minimizing clotting and tissue irritation.

Turning to catheter 12 of FIG. 1, this doublelumen catheter also defines lumens 18, 20, separated by wall 22. Alternatively, a concentric arrangement of double or multiple lumens may be provided to catheters of this invention, if desired.

As in the embodiment of catheter 10, lumen 20 of catheter 12 terminates at the catheter distal end in a first port 24a, while lumen 18 of catheter 12 terminates in second port 26a. As before, the catheter portion 28a between ports 24a and 26a is of helical shape, to prevent particularly second port 26a from engaging vein intima, to damage them by the suction pressure typically found in port 26a and its lumen 18. In this particular circumstance, the configuration of port 26a is different from port 26, in that port 26a is not inwardly angled as in the previous case of port 26. Rather, it is forwardly angled through a surface of the catheter wall which defines the base 48 of helical portion 28a. Thus, in this circumstance also, second port 26a faces away, to at least an extent, from the walls of vein 50, being also shielded from engagement with vein wall intima by the presence of helical portion 28a, which preferably has a diameter greater than the diameter of the remainder of catheter 12.

As in the previous embodiment, the flexible, resilient catheter 12 is shown in its as-manufactured, unstressed configuration, although it can be straightened our for packaging and insertion. Thus, as before, the catheter in its implanted position can exhibit little or no elastic memory that causes its distal end to press against the vein walls with resulting tissue irritation or damage and consequent generation of blood clots.

The remaining features of catheter 12 are similar to those of the previous catheter 10. Radiopaque stripe 40a and tissue adhesion cuffs 42a, 44a are provided for the same functions as in the previous embodiment The proximal portion 52 of catheter 12 extends out of tunnel entry site 11a, the tunnel which extends from tunnel exit 11a through the wall of vein 50 being formed by the surgeon.

In the arced area generally indicated by reference numeral 54, catheter 12 defines an angle of somewhat greater than 90 degrees. This angle is predetermined, plus the curvature of the arc of the catheter between cuff 42a and second port 26a, to accommodate to the shape of vein 50 with minimal vein wall contact.

Turning to FIG. 3, double lumen catheter 56 may be of a design that is substantially identical to that of catheter 10 except for the extent of the angle defined by angled section 58. This catheter is also shown in its asmanufactured, unstressed configuration, and defines almost a 180 degree angle throughout section 58 so that the catheter may be inserted through a surgical tunnel beginning at exit site 60, and then angled to proceed upwardly through the surgical tunnel to jugular vein 62, and then to permit the distal end 64 thereof to be angled downwardly again. The design of first and second ports 24b, 26b, and helical section 28b may be identical to the design of the corresponding components in catheter 10. Also, catheter 56 may carry a radiopaque stripe 40b and tissue securance cuffs 42b, 44b, for the purposes and advantages previously described.

Thus, in this embodiment also, the suction of blood through second port 26b and its connected lumen is performed with less risk of vein wall damage and consequent clotting and irritation, so that the catheter may function as a long-term indwelling catheter, to achieve the benefits for the dialysis patient as previously described.

FIG. 4 is another view of catheter 56, indwelling the jugular vein 62, taken 90 degrees from the viewpoint of FIG. 3. There, it can be seen that in section 64 of the catheter, the vein indwelling portion positioned between angled section 58 and second port 26b defines an arc in the dimension which is perpendicular to the plane defined by the angle in section 58. This is to provide improved compliance with the shape of the blood vessel including jugular vein 62 in which that length of catheter resides, particularly to avoid catheter pressure on a wall section of the venous system, such as wall portion 66.

Turning to FIGS. 5 and 6, the proximal end 68 of any of catheters 10, 12, 56, is shown, the proximal ends 68 of each catheter being identical to each other.

As shown in FIG. 6, the specific proximal catheter end 68 shown is a simple end of the catheter body which defines lumens 18, 20. A double ended, tubular prong member 70 is provided, being made of plastic or the like, having a central, enlarged handle portion 72 and a pair of connector tubes 74, 76, extending through handle portion 72 and projecting out both ends. The respective ends of tubular members 74, 76, are sized to respectively project at one end into lumens 18, 20, in tight, sealing relation. If desired, well known sealing ribs may be provided to the respective ends of tubes 74, 76.

Then, a connector extension member 78 may be provided. The particular connector extension member 78 shown includes a unitary connector base 80 defining a tube with a pair of lumens 82, 84, that are sized to engage their respective ends of connector tubes 74, 76, in a similar tight sealing manner as the opposed ends of connector tubes 74, 76.

Connector base 80 bifurcates into a pair of tubular connector extensions 86, 88, each of which defines a lumen 82, 84 and is terminated with a conventional connector 90, 92, to permit aseptic connection with a dialysis machine or the like, and also to permit connection with a sterile seal cap between uses. Connector 90 is shown to be closed off with a cap, while connector 92 has its cap removed.

Thus, as previously described, when connectors 90, 92, exhibit wear and need replacement before the indwelling catheter must be replaced, one can simply cut away connector member 78 by severing the proximal end of catheter 68 as proximally far out as possible. Then, a new connector link 70 and connector member 78 may be applied, to provide further useful life for the catheter system.

Referring to FIGS. 7 and 8, an alternative design of catheter 94 is disclosed. Only the distal tip is shown because the remainder of the catheter may be of a conventional design or in accordance with any of the previous embodiments disclosed herein.

Catheter 94 defines a pair of lumens 24c, 26c, which communicate with respective flow ports 24c, 26c, in a manner similar to the previous embodiments. It will be particularly noted that second port 26c is identical in configuration to second port 26 of FIGS. 1 and 1a, and exhibits described advantages of that particular design of second port.

An inflatable balloon 96 is carried on catheter 94, being connected to an inflation lumen 98 that may be of a diameter substantially less than that of the lumens that connect to ports 24c and 26c. Thus, as shown in FIG. 8, balloon 96 may be inflated after placement in a blood vessel 100. Balloon 96 is inflatable to a size which is large enough to limit engagement of second port 26c with the wall of blood vessel 100, but small enough to avoid complete occlusion of the blood vessel, as shown. Balloon 96 is shown diagrammatically, and may also be a conventional sleeve, sealed at both ends to the catheter, being made of a flexible but nonresilient material such as poly(ethylene terephthalate) or nylon.

Accordingly, substantial blood flow can still continue through vein 100, but second port 26c, serving as the blood inlet, is protected from engaging the blood vessel intima along its wall and causing damage through the suction pressure.

It should also be noted that the embodiment of FIGS. 7 and 8 may function in an effective manner without the presence of balloon 96 and lumen 98, relying merely upon the inwardly angled shape of second port 26c to avoid damaging engagement with the intima on the wall of blood vessel 100. Such an embodiment represents a simplified, inexpensive, and preferred embodiment of this invention, since it avoids the expense of fabricating and applying balloon 96 in the manufacture of the catheter, and it also avoids the expense involved in fabricating the helical distal catheter end 28 of the previous embodiments.

Accordingly, a multiple lumen catheter is provided for hemodialysis or any other desired use, which exhibits less clotting and irritation because it causes less damage to the walls of the blood vessel or duct in which it resides, when compared with other prior art catheters. Because of that, less clotting takes place as well, so that the catheter is capable of use as a long-term indwelling catheter for greater periods of time than other catheters of the prior art.

The above has been offered for illustrative purposes only, and is not intended to limit the scope of the invention of this application, which is as defined in the claims below.

That which is claimed is:

1. In a multiple lumen catheter for hemodialysis or the like, said catheter having a distal end portion in which at least a pair of the catheter lumens each communicate with the exterior through separate aperture means, the improvement comprising, in combination:

the aperture means of one of said lumens defining a first port at essentially the distal catheter end, and the aperture means of the other of said lumens defining a second port spaced proximally along the catheter from said distal end and first port, said second port being defined by a substantially annular wall having an outer portion relative to the catheter axis that is positioned slightly closer to said distal end than an inner portion of said substantially annular wall, whereby the axis of said second port is angled inwardly at an acute angle to catheter axis.

2. The catheter of claim 1 in which said one lumen comprises a portion that extends distally beyond said second port, said one lumen portion being defined by a distal catheter portion of substantially helical shape.

3. The catheter of claim 1 in which a section thereof, in its natural, unstressed configuration, defines an angle of at least about 90°, said section being spaced from and proximal to said second port.

4. The catheter of claim 3 in which a length of said catheter positioned between said angled section and said second port in its natural, unstressed configuration, defines an arc in the dimension perpendicular to the plane defined by the angle in said section, to provide improved compliance with the shape of the blood vessel in which said length of the catheter resides.

5. The catheter of claim 1 which defines an inflatable balloon positioned between said first and second ports, said balloon being inflatable to a size large enough to limit engagement of the second port with a wall of the blood vessel in which the catheter resides, but small enough to avoid complete occlusion thereof, and an inflation lumen in said catheter communicating with said balloon.

6. The catheter of claim 1 which comprises a pair of tubular connector extensions positioned at the proximal end thereof, and double-ended tubular prong means connecting each extension with one of said catheter lumens.

7. The catheter of claim 1 which carries a radiopaque stripe at least adjacent its distal end.

8. In a multiple lumen catheter for hemodialysis or the like, said catheter having a distal end portion in which at least a pair of the catheter lumens each communicate with the exterior through separate aperture means, the improvement comprising, in combination:

the aperture means of one of said lumens defining a first port at essentially the distal catheter end, and the aperture means of the other of said lumens defining a second port spaced proximally along the catheter from said distal end and first port, said second port being defined by a substantially annular wall having an outward portion relative to the catheter axis that is positioned slightly closer to said distal end than an inner portion of said substantially annular wall, whereby the axis of said second port is angled inwardly at an acute angle to the catheter axis; said one lumen comprising a portion that extends distally beyond said second port, said one lumen portion being defined in a distal catheter portion of substantially helical shape, said catheter having a section thereof which defines an angle of at least about 90°, said section being spaced from and proximal of said second port.

9. The catheter of claim 8 in which a length of said catheter positioned between said angled section and said second port, in its natural, unstressed configuration, defines an arc in the dimension perpendicular to the plane defined by the angle in said section, to provide improved compliance with the shape of a blood vessel in which said length of the catheter resides.

10. The catheter of claim 9 which comprises a pair of tubular catheter extensions positioned at the proximal end thereof, and double-ended, tubular prong means connecting each extension with one of said catheter lumens.

11. The catheter of claim 10 which carries a radiopaque stripe at lest adjacent its distal end.

12. In a multiple lumen catheter for hemodialysis or the like, said catheter having a distal end portion in which at least a pair of the catheter lumens each communicates with the exterior through aperture means, the improvement comprising, in combination;

the aperture means of one of said lumens defining a first port at essentially the distal catheter end, and the aperture means of the other of said lumens defining a second port spaced proximally along the catheter from said distal end and first port, said other lumen terminating at the second port, said one lumen comprising a portion that extends distally beyond said second port to be longitudinally spaced from the other of said lumens, said one lumen portion being defined in a distal catheter portion of substantially helical shape.

13. The catheter of claim 12 in which a section thereof, in its natural, unstressed configuration, defines an angle of at least about 90°, said section being spaced from and proximal of said second port.

14. The catheter of claim 13 in which a length of said catheter positioned between said angled section and said second port, in its natural, unstressed condition, defines an arc in the dimension perpendicular to the plane defined by the angle in said section, to provide improved compliance with the shape of a blood vessel in which said length of the catheter resides.

15. The catheter of claim 14 which comprises a pair of tubular connector extensions positioned at the proximal end thereof, and double-ended, tubular prong means connecting each extension with one of said catheter lumens.

16. The catheter of claim 15 which carries a radiopaque stripe at least adjacent its distal end.

17. The multiple lumen catheter of claim 12 in which said second port is positioned adjacent the proximal end of said helical distal catheter portion in a position to occupy a concave portion of said helical shape.

* * * * *